United States Patent [19]

Johnson

[11] 4,220,503
[45] Sep. 2, 1980

[54] STABILIZATION OF ACTIVATED GALACTOSE OXIDASE ENZYME

[75] Inventor: Jay M. Johnson, Dayton, Ohio

[73] Assignee: The Yellow Springs Instrument Co., Inc., Yellow Springs, Ohio

[21] Appl. No.: 901,144

[22] Filed: Apr. 28, 1978

[51] Int. Cl.³ .......................... C12Q 1/54; C12Q 1/26
[52] U.S. Cl. ...................................... 204/1 T; 435/25
[58] Field of Search ........... 204/1 T, 1 E, 1 P, 195 P, 204/195 B; 195/103.5 R, 103.5 C; 435/25, 26, 27, 28

[56] References Cited

U.S. PATENT DOCUMENTS

| | | | |
|---|---|---|---|
| 3,539,455 | 11/1970 | Clark | 204/195 P |
| 3,886,045 | 5/1975 | Meiattini | 195/103.5 |
| 3,947,328 | 3/1976 | Friedenberg et al. | 204/195 B |
| 3,979,274 | 9/1976 | Newman | 204/195 P |
| 4,073,713 | 2/1978 | Newman | 204/195 P |

FOREIGN PATENT DOCUMENTS 1442303 7/1976 United Kingdom .

OTHER PUBLICATIONS

Taylor et al., "Reprint from Analytical Chemistry", vol. 49, pp. 789-794, May 1977.
Amaral et al., "J. of Biological Chemistry", vol. 238 (1963) pp. 2281-2284.
"Journal of the Am. Chem. Soc.", 98:2 (1976), pp. 626-628.
Clark, "Annals of the New York Academy of Science", 102, (1962) pp. 29-45.
Clark, "Ion and Enzyme Electrodes in Biology and Medicine", Park Press, 1976, pp. 161-172.

Primary Examiner—G. L. Kaplan
Attorney, Agent, or Firm—Biebel, French & Nauman

[57] ABSTRACT

Galactose oxidase enzyme can effectively be used for the determination of a number of different substances if activated and stabilized in accordance with the present invention. Activation is accomplished with a redox agent such as ferricyanide. Stabilization of the activated galactose oxidase is accomplished by addition of cupric ion. Upon stabilization, activated, immobilized galactose oxidase enzymes may be stored and reused for at least 25 days.

13 Claims, No Drawings

STABILIZATION OF ACTIVATED GALACTOSE OXIDASE ENZYME

BACKGROUND OF THE INVENTION

This invention relates to a method for stabilizing activated galactose oxidase enzymes and, more particularly, it relates to a method for utilizing stabilized, activated galactose oxidase in the quantitative determination of unknowns which react with the galactose oxidase in a manner whereby a reactant or a product of the reaction may be analytically measured.

There are several types of analytical measurements which utilize enzymes. For example, in the determination of glucose, the enzyme glucose oxidase makes possible a number of types of analytical measurement. The reaction is as follows:

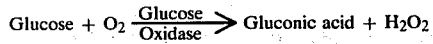

$$\text{Glucose} + O_2 \xrightarrow{\text{Glucose Oxidase}} \text{Gluconic acid} + H_2O_2$$

In a colorimetric method, the hydrogen peroxide produced, in turn, oxidizes a colorless chromogen to a dye in a catalyzed secondary reaction. As the catalyst in the secondary reaction, peroxidase can be utilized. A frequently employed chromogen is o-dianisidine. Spectrophotometry is used to measure the color change which takes place.

Enzymes have also been used in conjunction with polarographic cells, especially in instances where the unknown substance to be measured is not polarographically active, but a material produced or consumed by an enzymatic reaction with that unknown is detectable. For example, existence of the above-mentioned reaction involving glucose oxidase is significant in enabling polarographic measurement of glucose.

Thus, in an article by Clark and Lyons in the *Annals of the New York Academy of Science*, 102, 29–45 (1962), it was suggested that a pH sensitive electrode could be used to detect the gluconic acid produced by the reaction. It was disclosed that the enzyme in such a system could be trapped between Cuprophane membranes. The glucose diffuses through the membrane and is converted by the enzyme to gluconic acid, which then diffuses both toward the pH sensitive glass and back into the donor solution.

Alternatively, it was suggested that by using a hydrophobic membrane, a dialysis membrane, glucose oxidase, and a pO₂ electrode, a system could be arranged that is sensitive to glucose by virtue of the fact that oxygen is consumed from the flowing glucose solution in proportion to its glucose content.

Later, Clark obtained a patent on an improvement in such a system. In U.S. Pat. No. 3,539,455, it is stated that the system disclosed therein "differs in simplicity, reliability and in function from the cell disclosed in 'Annals of the New York Academy of Sciences'". Rather than measuring the pH change or the oxygen consumption, the Clark patent discloses using a platinum anode to measure the hydrogen peroxide produced. In the polarographic cell described in that patent, the enzyme is placed on the anode side of a cellophane membrane. The low molecular weight glucose passes through the membrane and reacts with the enzyme, but interfering high molecular weight catalase and peroxidase materials do not. It is disclosed that the enzyme may be held in a thin film directly between the platinum surface and the membrane by placing the enzyme on a porous film which has spaces large enough to hold enzyme molecules. The use of polymeric gels to stabilize the enzyme is also disclosed.

Finally, it is noted that Clark in U.S. Pat. No. 3,539,455 indicates that polarographic analysis can be used to determine substances other than glucose which are also acted upon by enzymes to yield hydrogen peroxide or other polarographically active substances. Among those mentioned by Clark are ascorbic acid, amino acids, galactose, etc. Since the Clark invention, others have effected polarographic determination of a number of such substances. Enzyme electrode measurements for glucose, amino acids, ethanol, cholesterol, phosphate, uric acid, and others have been reported. See, for example, L. C. Clark, Jr., and C. R. Emory in "Ion and Enzyme Electrodes in Biology and Medicine," Park Press, 1976, page 161.

In addition, efforts have been made to improve upon the Clark method for polarographic analysis. For example, the assignee of the present invention has developed certain novel laminated membranes for use in enzyme electrodes. These membrane structures are illustrated by U.S. Pat. Nos. 3,979,274 and 4,073,713 to Newman. The Newman patents relate to a thin laminated membrane comprising a layer of essentially homogeneous material such as cellulose acetate or silicone rubber which will prevent passage of even low molecular weight interfering materials, an adhesive layer including the enzyme, and a layer of support film which will also prevent the passage of high molecular weight interfering materials. Other membrane assemblies are shown in British Pat. No. 1,442,303 to Christiansen. In the Christiansen invention, the enzyme can be located at a number of possible locations in or on the membrane layers including bonding it chemically or mechanically either onto the outer surface of the membrane and in contact with a test solution or onto the inner surface of the membrane.

Accordingly, it can be said that there are several electrode-enzyme configurations possible. The enzyme may be either trapped between a membrane and an electrode, free in solution, or immobilized in or on the membrane. Immobilization, if possible, is the most desirable method as it allows prolonged reuse of the enzyme and greater reproducibility.

Galactose oxidase (D-galactose: O₂ oxidoreductose, EC 1.1.3.9) is one of the enzymes which it would be desirable to immobilize in an enzyme electrode in view of its ability to ultimately produce hydrogen peroxide from galactose, lactose and a number of other substances. Galactose measurement is important in the preliminary diagnosis of galactosemia and galactose intolerance. Also, research currently being conducted suggests that galactose may be an important alterntive energy source in premature infants and that the metabolism of galactose may impart some degree of regulation to blood glucose levels of diabetic infants.

One problem encountered in the use of the enzyme galactose oxidase is its relatively low level of enzymatic activity with some substances. For this reason, Hamilton et al in the Journal of the American Chemical Society, 98:2 (1976) at p. 626 have proposed activation by a redox material such as ferricyanide. Hamilton et al report as much as a three-fold increase in activity upon ferricyanide activation of galactose oxidase.

However, it has been found that in a system containing immobilized galactose oxidase and ferricyanide as an activator, the activity of the enzyme is rapidly lost (2–3 days). Whereas, the same system in the absence of ferricyanide maintains essentially constant enzyme activity over several days. Accordingly, the need exists for a means to activate the immobilized galactose oxidase and yet also stabilize the activated enzyme.

SUMMARY OF THE INVENTION

That need is met by the present invention in that it has been found that use of cupric ion along with the redox activator serves to stabilize the activated galactose oxidase enzyme. The redox (reduction-oxidation) activator may be any enzyme-compatable material capable of oxidizing the enzyme, and in the process being itself reduced. Examples are ferricyanide, iodate, dichromate, cobaltinitrite, and molybdate. Ferricyanide is preferred since it is the most compatable and stable. In oxidizing the galactose oxidase enzyme, ferricyanide is reduced to ferrocyanide.

The stabilized, activated galactose oxidase finds utility in a number of analytical measurement methods. Basically, it can be used in any system where the reaction of the galactose oxidase with the substance to be quantitatively determined produces a measurable reaction product or the disappearance of a reactant can be measured. In terms of the disappearance of a reactant, the polarographic measurement of oxygen consumption is a well-developed art.

In terms of the production of a reaction product, production of hydrogen peroxide with galactose oxidase is possible. The hydrogen peroxide production may then be measured in a colorimetric system by use of a peroxidase catalyzed secondary reaction with a o-dianisidine chromogen to give a dye measurable spectrophotometrically.

Most preferred, however, is a polarographic system for measuring the hydrogen peroxide production. In such a system, a membrane is used to prevent possible interfering materials from reaching the electrode.

The preferred membrane is a laminated one of the type disclosed in Newman U.S. Pat. Nos. 3,979,274 and 4,073,713, where the galactose oxidase enzyme is immobilized with glutaraldehyde between an inner and outer membrane layers. The inner layer (closest to the peroxide electrode) is the filter material such as cellulose acetate having a thickness of less than 2 microns. The outer layer (closest to the test solution) is a support material such as perforated polycarbonate having a thickness of between 1 and 20 microns. Of course, other membrane arrangements may also be used and the galactose oxidase enzyme may be immobilized anywhere in or on the membrane.

Actually, the galactose oxidase need not be immobilized but may be free in the test solution. However, it is preferred that it be immobilized since the stabilizing effect of the present invention is more important in regard to storage of an immobilized enzyme which is to be reused than it is with regard to one-time use of an enzyme free in a test solution which is discarded after use.

Thus, it is possible with the present invention to store immobilized activated galactose oxidase for several weeks and reuse it a number of times without significant loss of enzymic activity. This is due to stabilization with cupric ion. Preferably, the cupric ion is used in the test solution buffer along with redox activator. An example of an acceptable cupric ion is cupric chloride dihydrate.

The stabilization of activated galactose oxidase in this way means that in the preferred embodiment an enzyme electrode utilizing the stabilized-activated enzyme can be an economical and effective instrument in polarographic analysis. It is usable for quantitative determination of any number of substances which are effectively convertable by activated galactose oxidase enzyme to ultimately produce hydrogen peroxide which is polarographically measured.

As mentioned, it is also usable in situations where the hydrogen peroxide production is measured colorimetrically or even in situations where the disappearance of a reactant ($O_2$) is measured. Taking, for example, the measurement of galactose, the following reaction occurs:

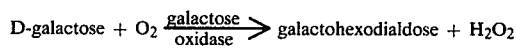

As can be seen, there are a number of known analytical methods for measuring either the production of the hydrogen peroxide or the uptake of oxygen in this reaction. As long as it involves the use of an activated enzyme which is also stabilized in accordance with this invention, efficient quantitative determinations are enabled.

Accordingly, it is an object of the present invention to provide a means for both activating and stabilizing galactose oxidase enzyme in order to produce an effective analytical determination of substances utilizing galactose oxidase enzyme.

Other objects and advantages of the invention will be apparent from the following description and the appended claims.

DESCRIPTION OF THE PREFERRED EMBODIMENT

For the purpose of illustrating the preferred embodiment, there will be discussed use of a stabilized-activated galactose oxidase enzyme electrode for the polarographic determination of galactose in plasma and whole blood. However, it should be realized that galactose oxidase is a non-specific enzyme and can be used to ultimately convert other substances to hydrogen peroxide. Accordingly, it is possible to use the stabilized-activated galactose oxidase enzyme electrode of the preferred embodiment in a number of other determinations.

Still, because of this, when testing a sample containing more than one substance reactive with galactose oxidase, it is not possible to get a quantative break-down for each substance. Therefore, caution must be exercised to prevent contamination of one substance which is to be determined with another reactive substance.

In the example to follow for the determination of galactose, the Model 23A analyzer of the assignee of the present invention was used. Although it is marketed as a dedicated glucose analyzer, the only requirement for its use in the measurement of any oxidizable substrate is the production of sufficient $H_2O_2$ by a specific oxidase to assure response by the hydrogen peroxide sensitive electrode. The basic principles of operation of such a polarographic analyzer are disclosed in Clark U.S. Pat. No. 3,539,455 which is hereby incorporated by reference.

Basically, there is utilized a cell assembly which includes an electrically insulating support body of plastic or glass. Positioned within the support body is an electrically insulating member or rod of plastic or glass which supports a platinum electrode, the latter including an active or exposed face.

The lower end of the support body is provided with an annular ring or retainer, and a preferred laminated membrane as described is supported over the end of the support body nearest the electrode and spaced a capillary distance from the active face. The membrane is held in position on the supporting body by an O-ring or the like.

An annular space is provided between the rod and the supporting body and receives a reference electrode which may for example be silver chloride coated silver wire. The space is at least partly and preferably completely filled with a liquid mixture of electrolyte which contacts both electrodes.

In polarographic measurements, two electrodes are commonly used, one of which is polarized and does not allow current to flow until depolarized by a substance being measured. Thus, the cathode may be polarized and is frequently referred to as the reference elctrode. The other electrode functions as an anode and is not polarized in the presence of the substances being measured and therefore will not restrict the flow of relatively large current and is frequently referred to as the sensor electrode. The electrodes are in electrically insulating relation, and the electrolyte material which occupies the chamber provides an electrical path between the two electrodes.

As mentioned, the membrane used in this preferred embodiment was a laminated one prepared essentially as described in U.S. Pat. Nos. 3,979,274 and 4,073,713. Galactose oxidase (D.galactose: $O_2$ oxidoreductase, EC 1.1.3.9) was immobilized between a thin cellulose acetate inner layer and a perforated polycarbonate outer layer (300-$A°$ pores) utilizing in the preferred form 0.29% glutaraldehyde.

After the galactose analyzer was calibrated with a 200 mg % (milligrams per 100 milliliters) galactose standard, various amounts of added substances were analyzed to determine if there was any response by the instrument. To determine whether the added substance had any effect on the enzyme activity of the electrode, 200 mg % standards were again analyzed in the presence of the substance being tested and any discrepancy from the expected result was noted.

Testing showed that enzyme-membrane activity was enchanced by a factor of approximately three in the presence of ferricyanide. Oxidizing agents, such as $NaIO_3$, $K_2Cr_2O_7$, $NaIO_4$, $K_3Co(NO_3)_6$ and $Na_2MoO_4.2H_2O$, were tried both singly and in combination, and, in general, behaved as did $K_3Fe(CN)_6$. However, none were as compatible and stable as ferricyanide. If the reduced forms of the oxidizing agents are allowed to reach the peroxide electrode, they will be oxidized and thus give a positive interference. The cellulose acetate filter membrane effectively blocks potassium ferricyanide from reaching the electrode.

However, in the presence of ferricyanide, the copper associated with galactose oxidase appeared to be more susceptible to complexing with ligands such as EDTA, if it is present in the buffer. At any rate, rapid loss of enzyme activity on storage was found. Since a gradual loss of copper and/or inactivation of the copper-enzyme site was suspected, a trace of copper in the form of cupric chloride dihydrate was added to the buffer. When this was done, all of the membranes tested were more active after 25 days storage and use than they were initially.

Utilizing the preferred buffer solution as described, i.e., containing 10 mg % $K_3Fe(CN)_6$ and 0.2 mg % $CuCl_2.2H_2O$, measurements for galactose in several "sample" solutions were made. The measurements of aqueous galactose standards in the region 0–500 mg % was linear. The slope of the least squares fit of the data is $5.00 \times 10^{-3}$ with a y-intercept of $-2.56 \times 10^{-3}$ and a correlation coefficient of 0.999. Increasing the concentration to 3000 mg % also produced a linear calibration curve. The slope of the least squares fit was $5.49 \times 10^{-3}$ with a y-intercept of $-0.16$ and a correlation coefficient of 0.998. All data points for both curves were the average of at least three determinations, each on a different membrane and instrument.

Plasma and whole blood samples, shown to be free of galactose, were spiked with galactose to known levels between 5 and 400 mg %. Both types of samples produced linear calibration curves. The least squares fit of the plasma data had a slope of 0.980, a y-intercept of 1.76 mg %, and a correlation coefficient of 0.999. Similarly, whole blood yielded a slope of 1.05, a y-intercept of $-1.81$ mg %, and a correlation coefficient of 0.999 when subjected to least squares treatment. Each data point represented the average of at least three determinations, each done on a different membrane and instrument. The pooled estimate of the standard deviation on the plasma and whole blood was 2.1 and 2.7 mg %, respectively.

The result was a rapid (40 sec), precise and accurate micromethod determination of galactose in the samples (both plasma and whole blood). More importantly, the immobilized galactose oxidase membranes are capable of being used and reused for a period of at least 25 days even in the presence of a redox activator as long as added cupric ions are also present. Since this allows a longer working life of the immobilized enzyme preparation with no sacrifice in measurement sensitivity, a method of quantitative polarographic determination with significant commercial potential is provided.

While the method herein described constitutes a preferred embodiment of the invention, it is to be understood that the invention is not limited to this precise method, and that changes may be made therein without departing from the scope of the invention.

What is claimed is:

1. In a method for the quantitative determination of a substance which reacts with a galactose oxidase enzyme in a manner whereby a reactant or a product of said reaction may be analytically measured and wherein said substance is introduced for determination by being included in a buffer solution which is brought into contact with said enzyme, said buffer solution also containing a sufficient amount of a reduction-oxidation agent to activate said enzyme, the improvement comprising adding to the buffer solution which contacts said galactose oxidase enzyme a sufficient amount of cupric ion to stabilize said activated enzyme whereby the stabilized, activated galactose oxidase enzyme may be reused and stored for a period of time after use without loss of its enzymic activity.

2. The method of claim 1 wherein said reaction ultimately produces hydrogen peroxide.

3. The method of claim 2 wherein said reduction-oxidation agent is ferricyanide.

4. The method of claim 3 wherein said hydrogen peroxide production is measured colorimetrically.

5. The method of claim 3 wherein said hydrogen peroxide production is measured polarographically.

6. A method for the quantitative polarographic determination of a polarographically inactive material which reacts with galactose oxidase enzyme in a manner whereby a reactant or a product of said reaction may be polarographically measured, comprising:
   (a) providing a polarographic cell including at least one electrode positioned behind a membrane permeable to the material being measured and in contact with an electrolyte,
   (b) establishing a potential across said cell such that a current is produced which is proportional to the amount of hydrogen peroxide or oxygen present on the electrode side of said membrane,
   (c) bringing said cell into contact with a quantity of material containing said polarographically inactive material in the presence of galactose oxidase enzyme and a buffer containing a reduction-oxidation agent
   said reduction-oxidation agent being present in said buffer in a sufficient amount to activate the galactose-oxidase enzyme,
   (d) adding to said buffer a sufficient amount of cupric ion to stabilize the activated enzyme, and
   (e) determining the current flowing across said cell as an indication of the amount of said substance present in said quantity of material.

7. The method of claim 6 wherein said galactose oxidase enzyme is immobilized in or on said membrane.

8. The method of claim 7 wherein said reduction-oxidation agent is ferricyanide.

9. The method of claim 8 wherein said polarographically inactive material is galactose.

10. The method of claim 9 wherein the determination of current flowing across said cell is a function of the amount of hydrogen peroxide formed.

11. The method of claim 10 wherein said galactose oxidase enzyme is immobilized with glutaraldehyde between an inner and outer membrane layer relative to said electrode.

12. The method of claim 11 wherein said inner layer is cellulose acetate and said outer layer is a perforated polycarbonate film.

13. The method of claim 12 wherein said buffer contains potassium ferricyanide in the approximate amount of 10 milligrams per 100 ml of buffer and cupric chloride dihydrate in the approximate amount of 0.2 milligrams per 100 ml of buffer.

* * * * *